United States Patent
Lu et al.

(10) Patent No.: US 10,131,941 B2
(45) Date of Patent: Nov. 20, 2018

(54) APPLICATION OF THIOLATED SINGLE-STRANDED DNA IN POLYMERASE CHAIN REACTION

(71) Applicant: INSTITUTE OF PLANT PROTECTION, SHANDONG ACADEMY OF AGRICULTRAL SCIENCES, JiNan, Shandong (CN)

(72) Inventors: Xingbo Lu, JiNan (CN); Guangyuan Zhang, JiNan (CN); Hongwei Sun, JiNan (CN); Fan Li, JiNan (CN); Shuke Yang, JiNan (CN); Rui Gao, JiNan (CN); Xiaohui Xu, JiNan (CN)

(73) Assignee: INSTITUTE OF PLANT PROTECTION, SHANDONG ACADEMY OF AGRICULTURAL SCIENCES, Shandong (CN)

( * ) Notice: Subject to any disclaimer, the term of this patent is extended or adjusted under 35 U.S.C. 154(b) by 401 days.

(21) Appl. No.: 14/648,870

(22) PCT Filed: Aug. 21, 2014

(86) PCT No.: PCT/CN2014/084885
§ 371 (c)(1),
(2) Date: Jun. 1, 2015

(87) PCT Pub. No.: WO2015/158088
PCT Pub. Date: Oct. 22, 2015

(65) Prior Publication Data
US 2016/0083778 A1    Mar. 24, 2016

(30) Foreign Application Priority Data
Apr. 18, 2014 (CN) .......................... 2014 1 0157936

(51) Int. Cl.
*C12Q 1/68* (2018.01)
*C12Q 1/686* (2018.01)
*C12Q 1/6844* (2018.01)
*C12N 15/11* (2006.01)
*C12Q 1/6848* (2018.01)

(52) U.S. Cl.
CPC .............. *C12Q 1/686* (2013.01); *C12N 15/11* (2013.01); *C12Q 1/6844* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 2005/0123937 A1* | 6/2005 | Thorp | B82Y 15/00 435/6.12 |
| 2011/0152346 A1 | 6/2011 | Karleson et al. | |
| 2013/0022682 A1* | 1/2013 | Lee | C12Q 1/6844 424/493 |

FOREIGN PATENT DOCUMENTS

| | | | | |
|---|---|---|---|---|
| CN | 1690216 A | | 11/2005 | |
| CN | 101983241 | * | 3/2011 | ........... C12N 15/113 |
| CN | 101983241 A | | 3/2011 | |
| CN | 102102125 A | | 6/2011 | |
| CN | 103993005 A | | 8/2014 | |
| WO | WO 2010017436 A2 | * | 2/2010 | ........... C12N 15/113 |

OTHER PUBLICATIONS

Lee, TM. et al. Sequence-specific electrochemical detection of asymetric PCR amplicons of traditional chinese medicinal plant DNA. Anal.Chem., vol. 74, p. 5057-5062, 2002.*
Patolsky F., et al. Redox-active nucleic-acid replica for the amplified bioeletrocatalytic detection of viral DNA. JACS, vol. 124, No. 5, p. 770-772, 2002.*
Hiep HM., et al. Nanostructured biochip for label-free and real-time optical detection of polymerase chain reaction. Analytica Chinnica Acta, vol. 661, p. 111-116, 2010.*
Cheung, MKL. et al. 5'-thiolated oligonucleotides on (3-mercaptopropyl)trimethoxysilane-mica: surface topography and coverage. Langmuir, vol. 19, p. 5846-5850, 2003.*
Jan. 19, 2015 International Search Report issued in Chinese Application No. PCT/CN2014/084885.

* cited by examiner

*Primary Examiner* — Suryaprabha Chunduru
(74) *Attorney, Agent, or Firm* — Oliff PLC

(57) ABSTRACT

An application of thiolated single-stranded DNA enhances specific amplification of polymerase chain reaction, namely a method for enhancing specific amplification of polymerase chain reaction by utilizing thiolated single-stranded DNA, which includes the following step: adding an appropriate amount of the thiolated single-stranded DNA into a PCR system to perform PCR amplification, wherein the appropriate amount means that the final concentration of the thiolated single-stranded DNA in a 20 μL reaction system is not less than 15 μM. The thiolated single-stranded DNA meets the following conditions: the thiolated single-stranded DNA is one segment of any sequence which is non-complementary and non-homologous to a target sequence; the Tm value is not less than 37.7° C.; and at least one end contains a thiolalkyl group SH—$C_6H_{12}$—.

4 Claims, 1 Drawing Sheet
Specification includes a Sequence Listing.

US 10,131,941 B2

APPLICATION OF THIOLATED SINGLE-STRANDED DNA IN POLYMERASE CHAIN REACTION

FIELD OF THE INVENTION

The present invention relates to an application of thiolated single-stranded DNA in enhancing specific amplification of polymerase chain reaction and belongs to the technical field of biology.

BACKGROUND OF THE INVENTION

Polymerase Chain Reaction (PCR), also known as in-vitro enzymatic gene amplification, is a nucleic acid amplification technology simulating natural DNA replication in vitro, has a very complex mechanism and can amplify target genes to a million times within a short period of time under the action of heat-resistant DNA polymerase and the guide of specific primers. The technology was invented by K. Mullis in 1983-1984 and has been widely applied in nucleic acid sequence analysis. After 30 years of development, PCR has been developed into a mature technology and has relatively small error rate in conventional experiments. However, in the actual applications, interference side reactions, such as base pair mismatch, amplification caused by formation of dimers between the primers and the like, often appear to a certain degree. These side reactions can cause non-specific amplification so as to result in low amplification efficiency when being slight, and cause amplification failure when being severe.

An important way for improving the specificity of the PCR amplification is to optimize the reaction components and the procedure of PCR. For many years in the past, many researchers made a lot of work in optimizing the reaction components of PCR, for example, the non-specific amplification problem can be avoided to a certain degree by adding DMSO, glycerine, betaine, nano-metals and the like into a reaction system. But in actual applications, some effects are not very ideal, for example, the excessive nano-metals and the like can inhibit the activity of the polymerase, thereby reducing the amplification efficiency.

By retrieval of existing patents and documents, it is found that the following contents are provided in Chinese patent application CN 101983241A: at least partially complementary modified (including thiol-modified and hydroxy-modified) oligonucleotide is subjected to strand hybridization with target nucleic acid, this way can be used for PCR amplification of the target nucleic acid, as it has been proved that more stable hydrogen bonding can occur between hydroxy nucleobases or thiol nucleobases and nucleobases in the target nucleic acid, the purposes of enhancing the modification sequence and the binding efficiency with a target sequence can be achieved. In the application mentioned in the patent application, the 'at least partially complementary modified oligonucleotide' is actually used as a primer in the PCR, the purpose of performing modification with hydroxy or thiol or other groups on the primer is to increase the binding efficiency of the primer with the target sequence and the primer does not have the function of enhancing the specificity of PCR.

SUMMARY OF THE INVENTION

With respect to the prior art, the present invention provides a method which can effectively enhance specific amplification of nucleic acid polymerase chain reaction, the method is realized by adding thiolated single-stranded DNA into a reaction system, and the method has a significant effect of optimizing the amplification and is simple in preparation, wide in range of applications, low in cost and easy to operate.

The present invention is implemented through the following technical solution:

an application of thiolated single-stranded DNA in polymerase chain reaction: through experimental researches, the applicant of the present invention proves that by adding thiolated oligonucleotide, namely thiolated single-stranded DNA into the PCR system, the optimization of the PCR system can be implemented: by adding an appropriate amount of thiolated single-stranded DNA into the PCR reaction system to perform PCR amplification, performing agarose gel electrophoresis detection on a product after amplification and comparing with an amplification product of the PCR system without adding the thiolated single-stranded DNA, and the results show that in the amplification product of the PCR system without adding the thiolated single-stranded DNA, the non-specific amplification is very serious, and in the amplification product of the PCR system with the thiolated single-stranded DNA, the non-specific amplification disappears completely and the specificity is obviously improved.

The thiolated single-stranded DNA refers to oligonucleotide with nucleotide at 5' or 3' end modified by thiolalkyl (SH—$C_6H_{12}$—), and the Tm value of the oligonucleotide needs to be not less than 37.7° C. (the Tm value is calculated by using biology software Oligo 7.4).

The thiolated single-stranded DNA has no specific requirements on the sequence of bases, has one segment of random sequence which is non-complementary to a target sequence, is not used as a primer in the PCR and does not produce a PCR product chain.

Further, the thiolated single-stranded DNA meets the following conditions: (1) the thiolated single-stranded DNA has one segment of any sequence which is non-complementary (non-homologous) to the target sequence; (2) the Tm value is not less than 37.7° C.; and (3) at least one end contains a thiolalkyl group (SH—$C_6H_{12}$—).

The thiolated single-stranded DNA can be synthesized by a biological company according to a primer synthesis method and subjected to thiol modification, wherein the methods are conventional methods.

The polymerase chain reaction refers to the commonly used PCR amplification in molecular biology, including conventional PCR, complex template PCR and the like. For the PCR system, please see the description of each commercial ExTaq polymerase.

A method for enhancing specific amplification of polymerase chain reaction by utilizing thiolated single-stranded DNA is as follows: adding an appropriate amount of the thiolated single-stranded DNA into a PCR reaction system to perform PCR amplification, wherein the appropriate amount means that the final concentration of the thiolated single-stranded DNA in a 20 μL reaction system is not less than 15 μM. For example, the commonly used PCR amplification procedure is set according to the prior art as follows: preheating at the temperature of 95° C. for 5 min; denaturing at the temperature of 95° C. for 30s, annealing at the temperature of 58° C. for 30s, extending at the temperature of 72° C. for 30s, and performing 35 cycles, wherein the number of cycles, the annealing temperature, the annealing time and the extending time can be appropriately changed according to different PCR instruments and different primers; and finally, extending at the temperature of 72° C. for 7 min.

Referring to the prior art, the agarose gel electrophoresis generally comprises the following steps:
(1) preparing 2% of agarose gel (containing a dyeing agent, namely ethidium bromide);
(2) spotting a PCR product and simultaneously pointing a molecular weight marker as control;
(3) applying voltage of 4-5V/cm and performing electrophoresis for 30 min; and
(4) performing gel imaging, and observing and analyzing results.

Compared with the existing method, the method for enhancing the specific amplification of the polymerase chain reaction by utilizing the thiolated single-stranded DNA has the advantages of significant optimization effect, simple and convenient preparation, a wide range of applications, low cost, easy operation and the like. The thiolated single-stranded DNA with good stability can be preserved at the temperature of 4° C. for a long time without degradation or inactivation, and is very convenient to use, and only the appropriate amount of the thiolated single-stranded DNA needs to be added into the PCR system. The thiolated single-stranded DNA used in the present invention does not depend on the sequence of the bases, so that the applicable range is wide, and the thiolated single-stranded DNA can be directly used for PCR amplification of various genes without targeted design. The PCR amplification method developed by the present invention can optimize a variety of PCR systems, is suitable for various types of PCR amplification and has huge potential application value in the fields of detection and cloning of genes, genetic analysis, medical diagnosis, gene chips and the like.

DETAILED DESCRIPTION OF THE EMBODIMENTS

Figure 1:
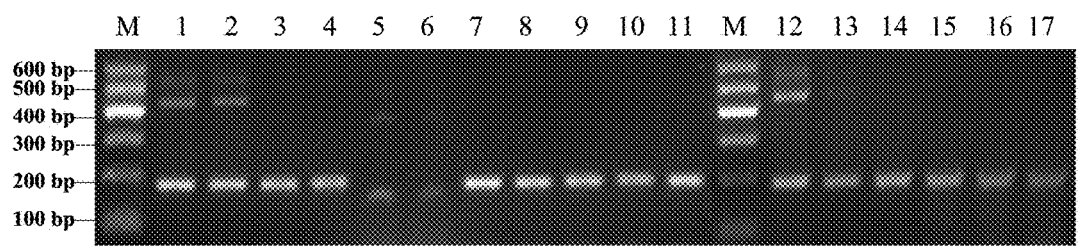
FIG. 1: an amplification optimization effect drawing of thiolated single-stranded DNA with regard to PCR amplification of a CaMV35S gene fragment in example 1.

The present invention is further described below in conjunction with examples.

Example 1

Optimization of Amplification of a CaMV35S Gene Fragment by Thiolated Single-stranded DNA (1) Configuration of a PCR System:

The reaction system contains 10 μL of 2× Premix ExTaq, 1 μL of each of an upstream primer and a downstream primer (10 μmol L$^{-1}$) (the sequences are as follows: F1: GCTCCTACAAATGCCATCATTGC and R1: GATAGTGGGATTGTGCGTCATCCC, as shown in SEQ ID NOs. 1 and 2), and 2 μL of DNA containing CaMV35S genes (total DNA from a genome of transgenic maize with CaMV35S), wherein Premix ExTaq is purchased from Dalian TaKaRa Company.

The configuration of each sample is as follows:

configure two tubes with the numbers of 1 and 2, wherein each tube adopts the conventional PCR system, and is supplemented with double-distilled water till the total volume is 20 μL;

configure 2 tubes with the numbers of 5 and 6, wherein each tube adopts a system with non-thiolated single-stranded DNA; and respectively add the non-thiolated single-stranded DNA into each tube till the final concentration is 20 μM, and further supplement each tube with the double-distilled water till the total volume is 20 μL, wherein the sequence of the non-thiolated single-stranded DNA is GTATGTGCCCATGTG, as shown in SEQ ID NO.3;

configure 7 tubes with the numbers of 3, 4, 7, 8, 9, 10 and 11, wherein each tube adopts the system with the thiolated single-stranded DNA; and respectively add the thiolated single-stranded DNA with the different sequence into each tube till the final concentration is 20 μM, and further supplement each tube with the double-distilled water till the total volume is 20 μL, wherein the sequences of the thiolated single-stranded DNA added into the tubes are as follows:

```
number 3:
HS-C₆H₁₂-GTATGTGCCCATGTG, with the nucleotide
sequence as shown in SEQ ID NO. 3;

number 4:
HS-C₆H₁₂-GTATGTGCCCATGTG, with the nucleotide
sequence which is the same as above;

number 7:
HS-ssDNA1:
HS-C₆H₁₂-CATACGCTCCAGACC, with the nucleotide
sequence as shown in SEQ ID NO. 4;

number 8
HS-ssDNA2:
HS-C₆H₁₂-GCCCTCTACTCCACC, with the nucleotide
sequence as shown in SEQ ID NO. 5;

number 9:
HS-ssDNA3:
HS-C₆H₁₂-ACAGCCTCACTGGAA, with the nucleotide
sequence as shown in SEQ ID NO. 6;

number 10:
HS-ssDNA4:
HS-C₆H₁₂-TGACTCCAICATCTGTT, with the nucleotide
sequence as shown in SEQ ID NO. 7;

number 11:
HS-ssDNA5:
HS-C₆H₁₂-TAGGACAATCCGTATCT, with the nucleotide
sequence as shown in SEQ ID NO. 8;
``` configure 6 tubes with the numbers of 12, 13, 14, 15, 16 and 17, wherein each tube adopts an optimization system added with the thiolated single-stranded DNA, the Tm values of the six tubes are 12.9° C., 30.3° C., 37.7° C., 47.4° C., 53° C. and 59.1° C. respectively, and the specific Tm values and the sequences of the added thiolated single-stranded DNA are as follows:

```
number 12:
12.9° C.;
HS-C₆H₁₂-GTATGTGC, with the nucleotide sequence
as shown in SEQ ID NO. 9;
```

-continued number 13:
30.3° C.;
HS-C$_6$H$_{12}$-GTATGTGCCC, with the nucleotide sequence as shown in SEQ ID NO. 10;

number 14:
37.7° C.;
HS-C$_6$H$_{12}$-GTATGTGCCCAT, with the nucleotide sequence as shown in SEQ ID NO. 11;

number 15:
47.4° C.;
HS-C$_6$H$_{12}$-GTATGTGCCCATGTG, with the nucleotide sequence as shown in SEQ ID NO. 3;

number 16:
53° C.;
HS-C$_6$H$_{12}$-GTATGTGCCCATGTGTTG, with the nucleotide sequence as shown in SEQ ID NO. 12;
and number 17:
59.1° C.;
HS-C$_6$H$_{12}$-GTATGTGCCCATGTGTTGCG, with the nucleotide sequence as shown in SEQ ID NO. 13.

(2) A PCR technology is utilized to amplify template molecules, and the amplification procedure is as follows: at 95° C. for 5 min; at 95° C. for 30s, at 58° C. for 30s, at 72° C. for 30s, and 35 cycles; and at 72° C. for 7 min.

(3) Agarose gel electrophoresis detection is performed on the DNA samples after amplification:

The amplification results are as shown in FIG. 1, wherein the samples corresponding to all lanes are as follows:
M: molecular weight markers (Marker I of Beijing Tiangen Company, which are 100 bp, 200 bp, 300 bp, 400 bp, 500 bp and 600 bp from bottom to top respectively);
1-2: conventional PCR system;
3-4: optimized improvement system added with thiolated single-stranded DNA;
5-6: control system added with non-thiolated single-stranded DNA;
7-11: optimized improvement systems with thiolated single-stranded DNA of HS-ssDNA1, HS-ssDNA2, HS-ssDNA3, HS-ssDNA4 and HS-ssDNA5 respectively;
12-17: optimized improvement systems which are added with thiolated single-stranded DNA with the Tm values of 12.9° C., 30.3° C., 37.7° C., 47.4° C., 53° C. and 59.1° C. respectively.

The amplified target gene fragment is of 195 bp. It can be seen from FIG. 1 that the serious non-specific amplification appears in the conventional PCR, which is represented by two non-specific bands (the sizes are about 450 bp and 550 bp respectively, lanes 1-2); and the non-specific amplification disappears completely in the PCR system added with the random thiolated single-stranded DNA with the Tm of not less than 37.7° C. (lanes 3-4, 7-11 and 14-17) while the non-specific amplification still exists in the control system which is added with the non-thiolated single-stranded DNA and thiolated single-stranded DNA with the Tm value of less than 37.7° C. (lanes 5-6, 12-13).

Example 2

Optimization of Amplification of a Complex Plant Genome, Namely Transgenic Maize MON810, by Thiolated Single-stranded DNA (1) Configuration of a PCR System:
The reaction system contains 10 μL of 2× Premix ExTaq, 1 μL of each of an upstream primer and a downstream primer (10 μmol L$^{-1}$) (the sequences are as follows: F1: CAAGTGTGCCCACCACAGC and R1: GCAAGCAAATTCGGAAATGAA, as shown in SEQ ID NOs. 14 and 15), and 2 μL of DNA containing a genome of transgenic maize MON810, wherein Premix ExTaq is purchased from Dalian TaKaRa Company.

The configuration of each sample is as follows:
configure three tubes with the numbers of 1, 2 and 3, wherein each tube adopts the conventional PCR system, and is supplemented with double-distilled water till the total volume is 20 μL;
configure three tubes with the numbers of 4, 5 and 6, wherein each tube adopts the system added with the thiolated single-stranded DNA; and respectively add the thiolated single-stranded DNA with the different sequence into each tube till the final concentration is 20 μM, and further supplement each tube with the double-distilled water till the total volume is 20 μL, wherein the sequences of the thiolated single-stranded DNA are as follows:

number 4:
HS-ssDNA1:
HS-C$_6$H$_{12}$-CATACGCTCCAGACC, with the nucleotide sequence as shown in SEQ ID NO. 4;

number 5:
HS-ssDNA2:
HS-C$_6$H$_{12}$-GCCCTCTACTCCACC, with the nucleotide sequence as shown in SEQ ID NO. 5;
and number 6:
HS-ssDNA3:
HS-C$_6$H$_{12}$-ACAGCCTCACTGGAA, with the nucleotide sequence as shown in SEQ ID NO. 6;

configure one tube with the number of 7, wherein the tube adopts a system added with non-thiolated single-stranded DNA; and add the non-thiolated single-stranded DNA into the tube till the final concentration is 20 μM, and further supplement each tube with the double-distilled water till the total volume is 20 μL, wherein the sequence of the non-thiolated single-stranded DNA is CATACGCTCCAGACC, as shown in SEQ ID NO. 4;
configure 6 tubes with the numbers of 8-13, wherein each tube adopts an optimization system added with the thiolated single-stranded DNA; and respectively add the thiolated single-stranded DNA with the Tm values of 12.9° C., 30.3° C., 37.7° C., 47.4° C., 53° C. and 59.1° C., wherein the specific Tm values and the sequences of the added thiolated single-stranded DNA are as follows:

number 8:
12.9° C.;
HS-C$_6$H$_{12}$-GTATGTGC, with the nucleotide sequence as shown in SEQ ID NO. 9;

number 9:
30.3° C.;
HS-C$_6$H$_{12}$-GTATGTGCCC, with the nucleotide sequence as shown in SEQ ID NO. 10;

number 10:
37.7° C.;
HS-C$_6$H$_{12}$-GTATGTGCCCAT, with the nucleotide sequence as shown in SEQ ID NO. 11;

number 11:
47.4° C.;
HS-C$_6$H$_{12}$-GTATGTGCCCATGTG, with the nucleotide sequence as shown in SEQ ID NO. 3;

-continued number 12:
53° C.;
HS-C$_6$H$_{12}$-GTATGTGCCCATGTGTTG, with the nucleotide sequence as shown in SEQ ID NO. 12;
and number 13:
59.1° C.;
HS-C$_6$H$_{12}$-GTATGTGCCCATGTGTTGCG, with the nucleotide sequence as shown in SEQ ID NO. 13.

(2) A PCR technology is utilized to amplify template molecules, and the amplification procedure is as follows: at 95° C. for 5 min; at 95° C. for 30s, at 58° C. for 30s, at 72° C. for 30s, and 35 cycles; and at 72° C. for 7 min.

Figure 2:
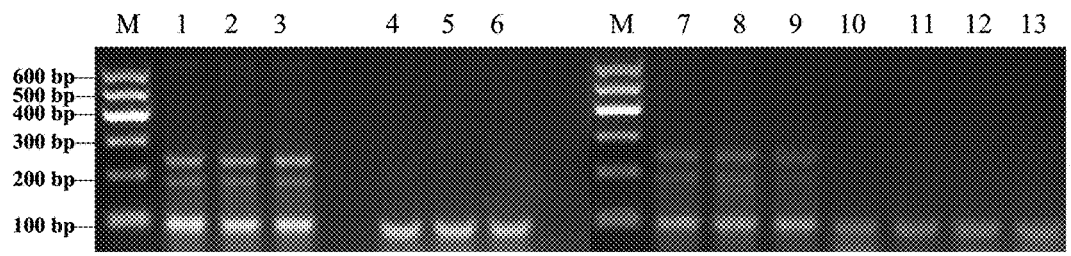
FIG. 2: an amplification optimization effect drawing of thiolated single-stranded DNA with regard to PCR amplification of a complex plant genome, namely transgenic maize MON810 in example 2.

(3) Agarose gel electrophoresis detection is performed on the DNA samples after amplification:

The amplification results are as shown in FIG. 2, wherein the samples corresponding to all lanes are as follows:

M: molecular weight markers (Marker I of Beijing Tiangen Company, which are 100 bp, 200 bp, 300 bp, 400 bp, 500 bp and 600 bp from bottom to top respectively);

1-3: conventional PCR system;

2: optimized improvement system added with the random non-homologous thiolated single-stranded DNA with Tm of 0° C. (GTATGT);

4-6: optimized improvement systems added with thiolated single-stranded DNA of HS-ssDNA1, HS-ssDNA2 and HS-ssDNA3 respectively;

7: control system added with non-thiolated single-stranded DNA with the sequence of CATACGCTCCAGACC;

8-13: optimized improvement systems which are added with thiolated single-stranded DNA with the Tm values of 12.9° C., 30.3° C., 37.7° C., 47.4° C., 53° C. and 59.1° C. respectively.

The amplified target gene fragment is of 106 bp. It can be seen from FIG. 2 that the serious non-specific amplification appears in the conventional PCR, which is represented by two non-specific bands (about 200 bp respectively, lanes 1-3); and the non-specific amplification disappears completely in the PCR system added with the random thiolated single-stranded DNA with the Tm of not less than 37.7° C. (lanes 4-6, and 10-13) while the non-specific amplification still exists in the control system which is added with the non-thiolated single-stranded DNA and the thiolated single-stranded DNA with the Tm value of less than 37.7° C. (lanes 7-9).

The invention claimed is:

1. A method for enhancing specific amplification of polymerase chain reaction, the method comprising:

adding thiolated single-stranded DNA into a PCR system, the thiolated single-stranded DNA consisting of a oligonucleotide with thiolated nucleotide at at least one end thereof; and performing PCR amplification in the presence of the thiolated single-stranded DNA in the PCR system to obtain an amplification product of the PCR system; wherein the thiolated single-stranded DNA includes at least one of the following sequences selected from the group consisting of:

HS-$C_6H_{12}$-GTATGTGCCCATGTG, with the nucleotide sequence as shown in SEQ ID NO. 3;

HS-ssDNA1:
HS-$C_6H_{12}$-CATACGCTCCAGACC, with the nucleotide sequence as shown in SEQ ID NO. 4;

-continued

HS-ssDNA2:
HS-C$_6$H$_{12}$-GCCCTCTACTCCACC, with the nucleotide
sequence as shown in SEQ ID NO. 5;

HS-ssDNA3:
HS-C$_6$H$_{12}$-ACAGCCTCACTGGAA, with the nucleotide
sequence as shown in SEQ ID NO. 6;

HS-ssDNA4:
HS-C$_6$H$_{12}$-TGACTCCATCATCTGTT, with the nucleotide
sequence as shown in SEQ ID NO. 7;

HS-ssDNA5:
HS-C$_6$H$_{12}$-TAGGACAATCCGTATCT, with the nucleotide
sequence as shown in SEQ ID NO. 8;

HS-C$_6$H$_{12}$-GTATGTGC, with the nucleotide sequence
as shown in SEQ ID NO. 9;

HS-C$_6$H$_{12}$-GTATGTGCCC, with the nucleotide sequence
as shown in SEQ ID NO. 10;

HS-C$_6$H$_{12}$-GTATGTGCCCAT, with the nucleotide
sequence as shown in SEQ ID NO. 11;

HS-C$_6$H$_{12}$-GTATGTGCCCATGTGTTG, with the nucleotide
sequence as shown in SEQ ID NO. 12;
and HS-C$_6$H$_{12}$-GTATGTGCCCATGTGTTGCG, with the nucleotide
sequence as shown in SEQ ID NO. 13.

2. The method according to claim 1, wherein:
the Tm value of the thiolated single-stranded DNA is not less than 37.7° C.; and
the thiolated nucleotide at at least one end of the thiolated single-stranded DNA contains a thiolalkyl group SH—C$_6$H$_{12}$—.

3. The method according to claim 1, wherein the step of performing PCR amplification comprises:
adding an appropriate amount of the thiolated single-stranded DNA into the PCR system to perform PCR amplification in a 20 μL reaction system, the appropriate amount being a final concentration of the thiolated single-stranded DNA of not less than 15 μM in the 20 μL reaction system.

4. A method for enhancing specific amplification of polymerase chain reaction (PCR) by utilizing thiolated single-stranded DNA, the method comprising:
adding an appropriate amount of the thiolated single-stranded DNA into a PCR system to perform PCR amplification, the thiolated single-stranded DNA consisting of a oligonucleotide with thiolated nucleotide at at least one end thereof; and
performing PCR amplification in the PCR system; wherein
the appropriate amount means that the final concentration of the thiolated single-stranded DNA in a 20 μL reaction system is not less than 15 Mm; and
the thiolated single-stranded DNA includes at least one of the following sequences selected from the group consisting of:

HS-C$_6$H$_{12}$-GTATGTGCCCATGTG, with the nucleotide
sequence as shown in SEQ ID NO. 3;

HS-ssDNA1:
HS-C$_6$H$_{12}$-CATACGCTCCAGACC, with the nucleotide
sequence as shown in SEQ ID NO. 4;

HS-ssDNA2:
HS-C$_6$H$_{12}$-GCCCTCTACTCCACC, with the nucleotide
sequence as shown in SEQ ID NO. 5;

HS-ssDNA3:
HS-C$_6$H$_{12}$-ACAGCCTCACTGGAA, with the nucleotide
sequence as shown in SEQ ID NO. 6;

HS-ssDNA4:
HS-C$_6$H$_{12}$-TGACTCCATCATCTGTT, with the nucleotide
sequence as shown in SEQ ID NO. 7;

HS-ssDNA5:
HS-C$_6$H$_{12}$-TAGGACAATCCGTATCT, with the nucleotide
sequence as shown in SEQ ID NO. 8;

HS-C$_6$H$_{12}$-GTATGTGC, with the nucleotide sequence
as shown in SEQ ID NO. 9;

HS-C$_6$H$_{12}$-GTATGTGCCC, with the nucleotide sequence
as shown in SEQ ID NO. 10;

HS-C$_6$H$_{12}$-GTATGTGCCCAT, with the nucleotide
sequence as shown in SEQ ID NO. 11;

HS-C$_6$H$_{12}$-GTATGTGCCCATGTGTTG, with the nucleotide
sequence as shown in SEQ ID NO. 12;
and HS-C$_6$H$_{12}$-GTATGTGCCCATGTGTTGCG, with the
nucleotide sequence as shown in SEQ ID NO. 13.

* * * * *

SEQUENCE LISTING

```
<160> NUMBER OF SEQ ID NOS: 15

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1
gctcctacaa atgccatcat tgc                                          23

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
gatagtggga ttgtgcgtca tccc                                         24

<210> SEQ ID NO 3
<211> LENGTH: 15
<212> TYPE: DNA
<213> ORGANISM: Artificial Sequence
<220> FEATURE:
<223> OTHER INFORMATION: Synthetic Construct

<400> SEQUENCE: 3
gtatgtgccc atgtg                                                   15

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct

<400> SEQUENCE: 4
```

-continued catacgctcc agacc                                                 15

<210> SEQ ID NO 5
<211> LENGTH: 15
<212> TYPE: DNA
<213> ORGANISM: Artificial Sequence
<220> FEATURE:
<223> OTHER INFORMATION: Synthetic Construct

<400> SEQUENCE: 5
gccctctact ccacc                                                 15

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct

<400> SEQUENCE: 6
acagcctcac tggaa                                                 15

<210> SEQ ID NO 7
<211> LENGTH: 17
<212> TYPE: DNA
<213> ORGANISM: Artificial Sequence
<220> FEATURE:
<223> OTHER INFORMATION: Synthetic Construct

<400> SEQUENCE: 7
tgactccatc atctgtt                                               17

<210> SEQ ID NO 8
<211> LENGTH: 17
<212> TYPE: DNA
<213> ORGANISM: Artificial Sequence
<220> FEATURE:
<223> OTHER INFORMATION: Synthetic Construct

<400> SEQUENCE: 8
taggacaatc cgtatct                                               17

<210> SEQ ID NO 9
<211> LENGTH: 8
<212> TYPE: DNA
<213> ORGANISM: Artificial Sequence
<220> FEATURE:
<223> OTHER INFORMATION: Synthetic Construct

<400> SEQUENCE: 9 gtatgtgc                                                          8

<210> SEQ ID NO 10
<211> LENGTH: 10
<212> TYPE: DNA
<213> ORGANISM: Artificial Sequence
<220> FEATURE:
<223> OTHER INFORMATION: Synthetic Construct

```
<400> SEQUENCE: 10
gtatgtgccc                                                          10

<210> SEQ ID NO 11
<211> LENGTH: 12
<212> TYPE: DNA
<213> ORGANISM: Artificial Sequence
<220> FEATURE:
<223> OTHER INFORMATION: Synthetic Construct

<400> SEQUENCE: 11
gtatgtgccc at                                                       12

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct

<400> SEQUENCE: 12
gtatgtgccc atgtgttg                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
gtatgtgccc atgtgttgcg                                               20

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
caagtgtgcc caccacagc                                                19

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
gcaagcaaat tcggaaatga a                                             21
```